United States Patent [19]

Blanck

[11] Patent Number: 5,793,835
[45] Date of Patent: Aug. 11, 1998

[54] QUALITY ASSURANCE PHANTOM FOR TOMOGRAPHY AND METHOD OF USE

[76] Inventor: Cheryl A. Blanck, 560 Peoples Plz. Suite 106, Newark, Del. 19701

[21] Appl. No.: 822,566

[22] Filed: Mar. 19, 1997

[51] Int. Cl.⁶ ............................................. A61B 6/03
[52] U.S. Cl. ............................. 378/4; 378/18; 378/207
[58] Field of Search .................................. 378/4, 18, 207

[56] References Cited

U.S. PATENT DOCUMENTS

| | | | |
|---|---|---|---|
| 3,010,223 | 11/1961 | Alderson | 35/17 |
| 3,509,337 | 4/1970 | DeClerk et al. | 250/61.5 |
| 4,055,771 | 10/1977 | Goodenough et al. | 378/145 |
| 4,126,789 | 11/1978 | Vogl et al. | 250/505 |
| 4,344,183 | 8/1982 | Jacobson | 378/207 |
| 4,352,020 | 9/1982 | Horiba et al. | 378/18 |
| 4,646,334 | 2/1987 | Zerhouni | 378/18 |
| 4,663,772 | 5/1987 | Mattson et al. | 378/18 |
| 4,873,707 | 10/1989 | Robertson | 378/18 |
| 4,962,514 | 10/1990 | Hart et al. | 378/18 |
| 5,056,130 | 10/1991 | Engel | 378/207 |
| 5,164,978 | 11/1992 | Goodenough et al. | 378/207 |
| 5,165,050 | 11/1992 | Goodenough et al. | 324/318 |
| 5,222,021 | 6/1993 | Feldman et al. | 378/18 |
| 5,416,816 | 5/1995 | Wenstrup et al. | 378/18 |
| 5,506,884 | 4/1996 | Goodenough et al. | 378/207 |

*Primary Examiner*—David P. Porta
*Attorney, Agent, or Firm*—Oldham & Oldham Co., L.P.A.

[57] ABSTRACT

A quality assurance test phantom having a shell wherein water and test objects reside in conjunction with a bellows capable of longitudinally translating one or more of a variety of test objects within the inside of the phantom via a screw mechanism is described. These test objects are employed in novel tests to quantitatively evaluate the imaging performance of a computed tomography ("CT") device with specific regard to the construction of pseudo-planar slices produced from scan data taken using helical scanning techniques.

19 Claims, 3 Drawing Sheets

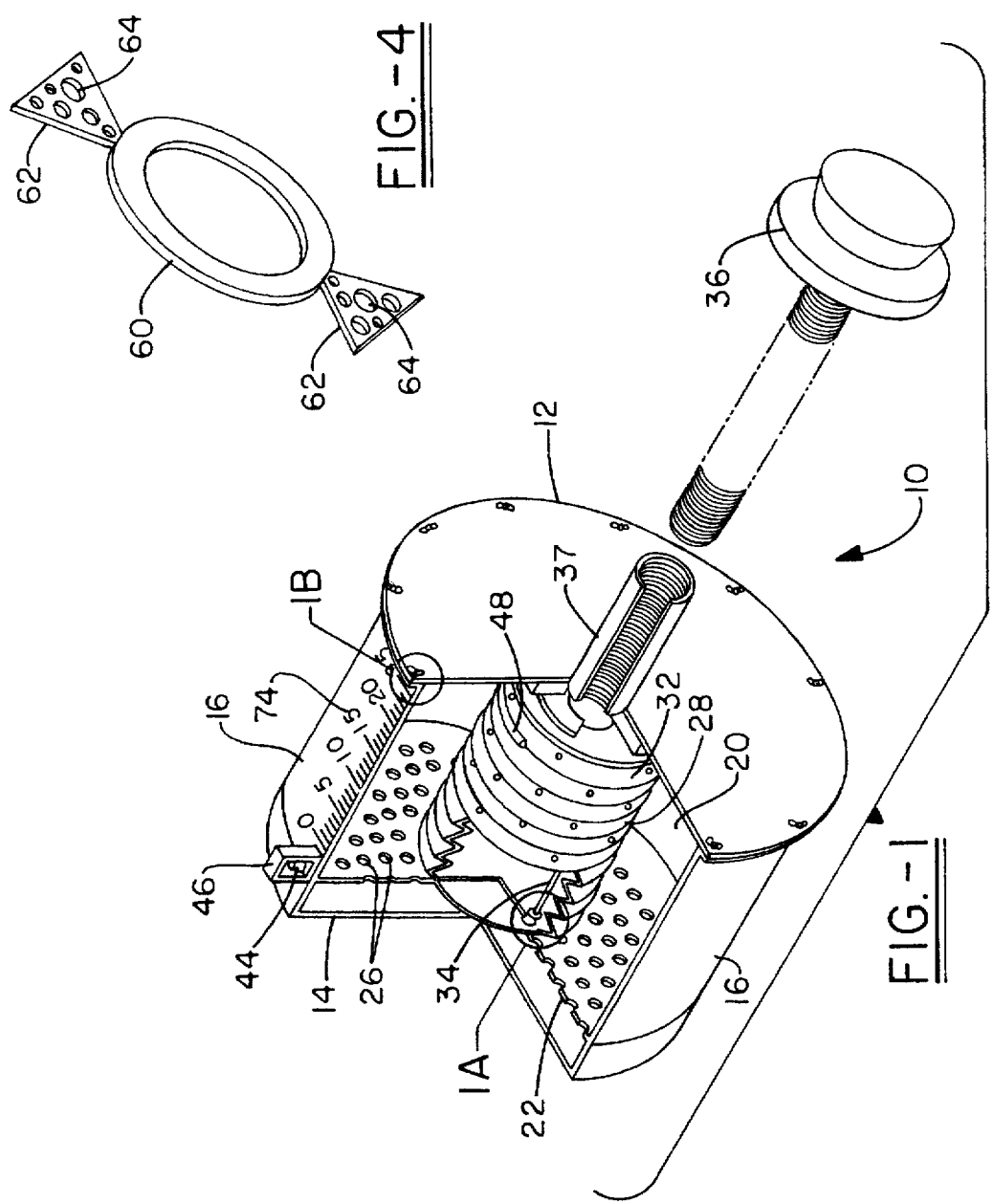
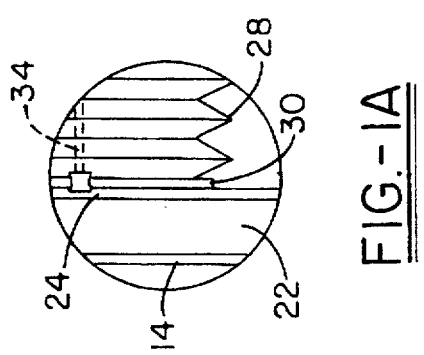
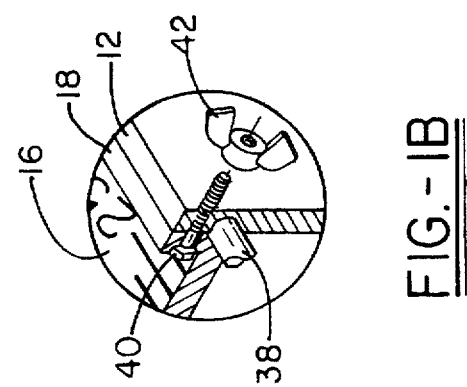

QUALITY ASSURANCE PHANTOM FOR TOMOGRAPHY AND METHOD OF USE

The present invention relates to the field of computed tomography and, in particular, to a unique calibration phantom and test methods useful for quantifying the operating characteristics of a helical tomographic imaging apparatus.

BACKGROUND OF THE ART

The first scanning and mathematical reconstruction method developed in association with computed tomography (CT) systems was the conventional or "axial" scanning technique. In this technique, an image of an object is produced by using a radiation source which rotates in an equidistant circular path around the object. The image, which is reconstructed from scan data, represents the attenuation of an x-ray beam passing through the object, which has x, y and z axes. The radiation from the x-ray source passing through the object is collected on a diametrically opposed detection array such that, for a given position along the z-axis (or longitudinal plane) of the object, a single cross-sectional image of the object is reconstructed from a particular acquired data set. To produce another image at another longitudinal position in the object, the object must be moved or indexed and another set of data acquired through an additional pass of the x-ray beam. Rather than moving the object, or in the medical sense, the patient, the preferred method of imaging is to position the object on a stationary patient support device generally known as the patient couch and to move or index the patient couch. It is important to note that the couch is only moved while the x-ray source is stationary and that the x-ray source only moves while the patient couch is stationary. The cross-sectional image (or "slice") representing the object's attenuation of the x-ray beam in the x-y plane for a given position along the z axis is then created by well-defined tomographic reconstruction techniques. Subsequent imaging passes by the radiation source produces axially adjacent images of the x-y plane of the object.

A newer technology known variously as volume scanning, helical scanning or spiral scanning does not gather data in the discrete axial sets of the "axial" technique just described. Instead, the patient couch moves smoothly and continuously in the axial direction (along the z-axis) while the radiation source moves in its equidistant circular path normal to the z-axis. This acquisition method produces a data set which is a continuous or "seamless" helical volume. Because of the difference in the data collection method, additional processing of the helical data is necessary prior to reconstruction. This additional processing is known as helical interpolation. Helical interpolation is used to prepare the helical data such that an image similar to that created from the axial scan data of the older technique can be created without obvious image blurring due to the linear movement of the patient.

In either "axial" or helical scanning, the system comprises the radiation source, the detection array, the motion controllers and the image interpolation hardware and software. The system must be calibrated to evaluate the result obtained. Calibration and quality assurance devices, known commonly as "phantoms", are used in assessing the imaging capabilities of CT systems. These phantoms are routinely centered in the scan field of the system and imaged. There are numerous examples of CT phantoms for axial scanning in the prior art.

Ideally, images produced using helical scanning should be identical to images obtained using axial scanning. However, helical and axial images of the same object are not identical. A variety of factors influence helical imaging and it is useful to define some of the terms used in association with this technique. "Pitch" refers to the axial distance that the patient couch moves longitudinally per revolution of the X-ray tube during data acquisition. The "slice thickness" is the width of the X-ray beam, which is determined by the collimator "thickness" setting. "Pitch ratio" is defined as the distance the patient couch is moved during one helical revolution divided by the slice thickness. The "scan speed" is the time necessary for the X-ray tube to complete one revolution around the subject. "CT number" is a measure of the attenuation of the ionizing radiation by a material and is established on a relative basis, using water as a reference or base attenuation. In addition to these machine factors, the characteristics of the object such as the presence of bone/tissue interfaces is also crucial in affecting the quality of an image produced from helical scan data.

While traditional tests designed to be used with axial scanning can be utilized to examine some of the more conventional elements of volume systems, a new testing device and methods need to be developed which would specifically measure a system's helical functionality by examining the interaction of various parameters unique to helical scanning.

SUMMARY OF THE INVENTION

It is therefore, an object of the present invention to provide a device for calibrating a helical CT scanner, as well as useful methods for using the device to calibrate such a helical scanner. Such an object is achieved by a device for calibrating a computed tomography apparatus, comprising a housing having first and second end walls and at least one side wall, an intermediate wall between said first and second end walls, effectively forming first and second chambers within said housing, a longitudinal translator axially mounted within said housing, said longitudinal translator having a first end thereof axially affixed to the intermediate wall; and a longitudinal translator adjustment screw axially mounted through a threaded opening in said first end wall with a first end thereof affixed to a second end of the longitudinal translator such that rotation of a second end of the longitudinal translator adjustment screw external to the housing results in axial movement of the second end of the longitudinal translator within the housing.

In a preferred embodiment, the housing is generally cylindrical with the side wall being a cylinder and at least the first of the end walls is removably affixed to the side wall, so that the end walls are affixable to the side wall in a water-tight manner.

In the preferred embodiment, the intermediate wall is provided with at least one aperture to communicate the first and second chambers. Further, the longitudinal translator is a bellows having first and second ends, a pleated generally cylindrical body between said ends, the body having apertures to communicate the inside of the bellows to the outside of the bellows, with the bellows being supported along a longitudinal axis of the housing by at least two spaced apart bellows stabilizer rods affixed to the intermediate wall, spanning the length of the first chamber, and received in the first end wall. In such an embodiment, at least one pleat of the bellows body is provided with a piece of material which has a substantially higher attenuation to x-rays than the attenuation of the housing, walls, bellows and adjustment screw, such as would be provided by a piece of wire when the housing, walls, bellows and adjustment screw are comprised of a polymeric material.

3

In the preferred embodiments, the exterior surface of the bellows body is adapted for affixing at least one test object thereto such that rotation of the adjustment screw results in longitudinal movement of the test object within the first chamber and the interior surface of the bellows body is adapted for affixing at least one test object thereto such that rotation of the adjustment screw results in longitudinal movement of the test object within the bellows body. Additionally, the inner surface of the side wall is preferred to be sized to frictionally receive and retain a generally hoop-shaped test object.

In the preferred embodiment, the second chamber is an essentially hollow cylinder.

A first test object for use with is device comprises a polymeric disc having first and second opposing surfaces with a centrally positioned circular piece of metallic foil affixed on the first surface thereof, said piece of metallic foil having an outside diameter smaller than the outside diameter of the polymeric disc, especially where the polymeric disc further comprises at least one aperture communicating the first and second surfaces thereof.

A second test object for use with the device comprises an annular disc comprising a low attenuation material having a plurality of equally spaced apart apertures of uniform diameter passing through the disc from a first planar surface thereof to an opposing second planar surface; and an inside periphery of the annular disc being adapted for affixation to a cylindrical body having an outside diameter slightly smaller than the inside diameter of said annular disc.

A third test object for a computed tomography apparatus calibration device comprises an annular disc having an inside diameter and an outside diameter, the periphery at said outside diameter having at least two apertures for removably affixing planar test elements of a known attenuation value, each said planar test element further having at least one aperture passing therethrough with one of said at least one aperture being of a known diameter; and an inside periphery of the annular disc being adapted for affixation to a cylindrical body having an outside diameter slightly smaller than the inside diameter of said annular disc.

A fourth test object for a computed tomography apparatus calibration device comprises a generally hoop-shaped disc having an inside diameter and an outside diameter and comprising a material of known attenuation, the inside diameter having a plurality of radially oriented apertures for removably affixing along said inside diameter at least one test element of a known attenuation value simulating a type of human bone, wherein each such test element has a male member for insertion in said aperture in a frictional fit and a visually distinctive profile dependent upon the attenuation value.

In a preferred embodiment of the present invention, the user would be provided with the phantom device and at least one of each of the four test objects, for performing a variety of calibration tests on the computed tomography apparatus.

BRIEF DESCRIPTION OF THE DRAWINGS

The present invention will be better understood when reference is made to the accompanying drawings, wherein identical parts are identified by identical reference numerals and wherein:

FIG. 1 is a perspective view of the phantom of the present invention, with enlarged areas showing items of interest in better detail;

4

Figure 2:
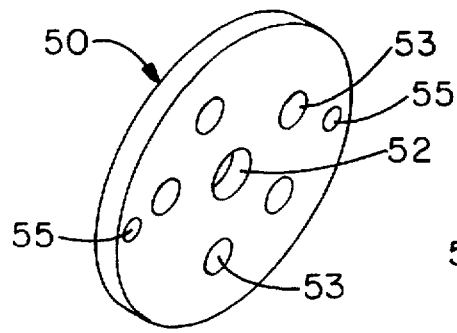
FIG. 2 shows a first test object of the present invention in perspective view in isolation.
Figure 2A:
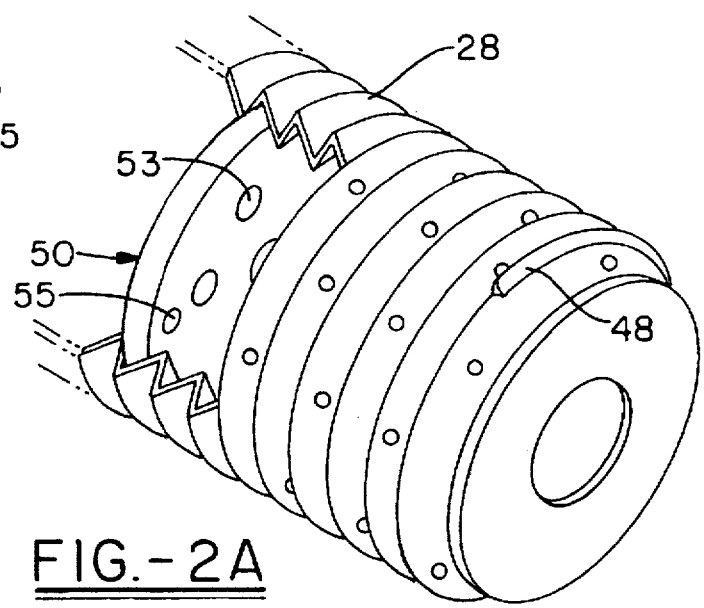
Figure 3:
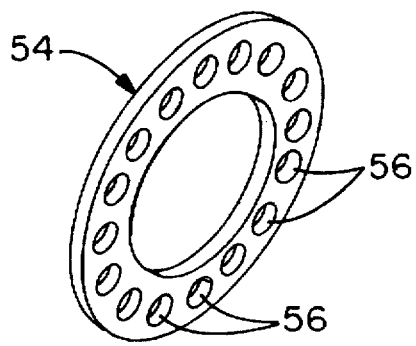
Figure 3A:
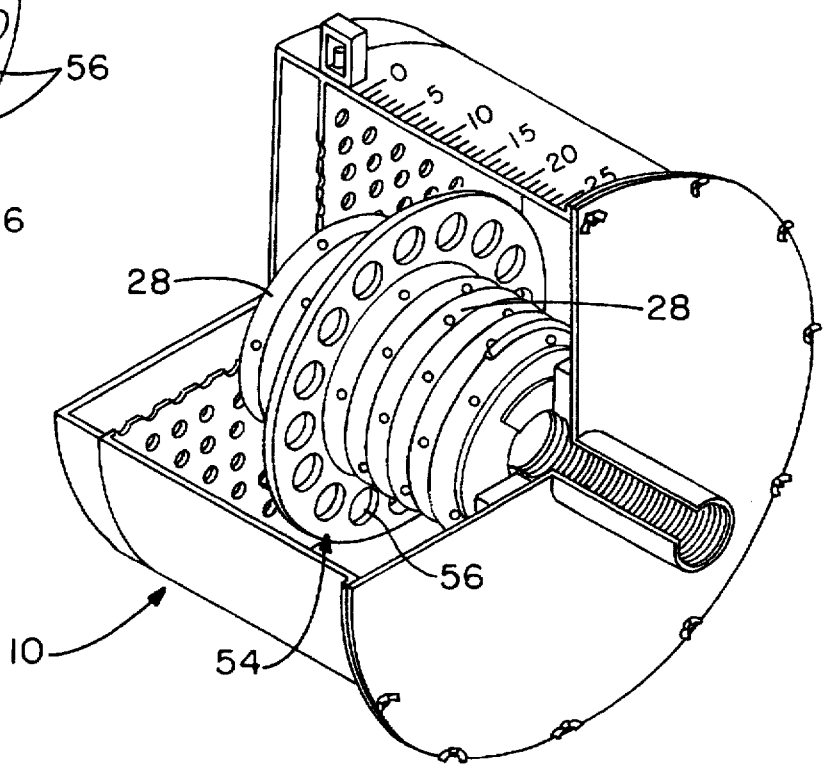
Figure 5:
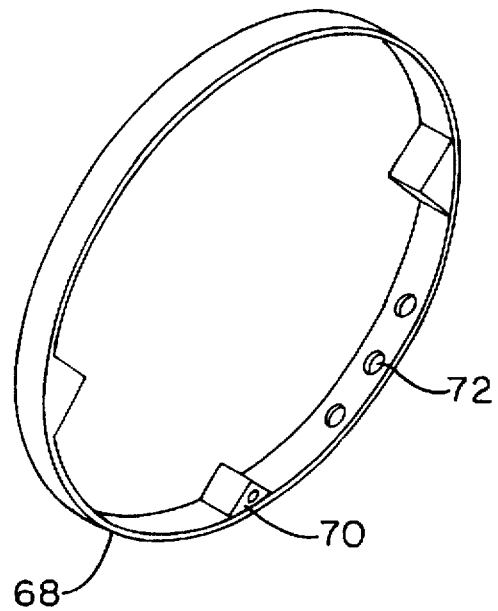
Figure 5A:
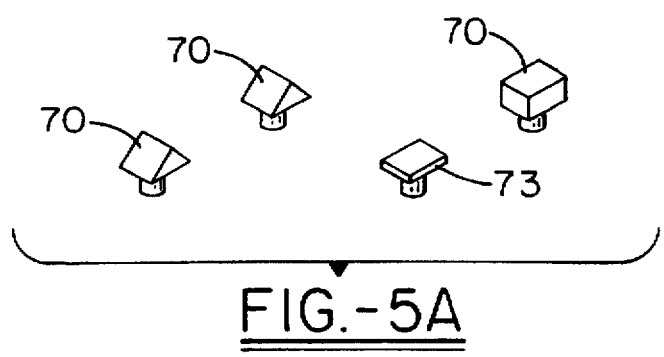

FIG. 2a shows the first test object operatively engaged inside the bellows of the present invention;

FIG. 3 shows a second test object of the present invention in perspective view in isolation;

FIG. 3a shows the second test object operatively engaged inside the phantom of the present invention;

FIG. 4 shows a third test object of the present invention in perspective view in isolation; and FIG. 5 shows a fourth test object of the present invention in isolated perspective view.

DETAILED DESCRIPTION OF THE PREFERRED EMBODIMENT

The phantom 10 of the present invention is presented in a perspective view in FIG. 1 and the enlargements of portions thereof presented therewith. The phantom 10 generally comprises a housing having a first end wall 12, a second end wall 14 and a side wall 16, preferably a housing which is cylindrical and which has a central axis of symmetry. In the particular embodiment illustrated, the first end wall 12 is removably affixed to a flange 18 provided around a first end of the side wall 16. The second end wall 14 is permanently affixed to a second end of the side wall 16, although the second end wall could be affixed to the second end of the side wall through a corresponding flange if so desired. The interior of the housing is divided into first and second chambers 20, 22 of fixed volume by an internal wall 24 positioned essentially parallel to the first and second end walls 12, 14 internal to the housing and affixed about its periphery to the side wall 16. Of these chambers, the first chamber 20 is shown in FIG. 1 as being volumetrically larger than the second chamber 22, since the internal wall 24 is closer to the second end wall 14 than to the first end wall 12. As also shown in FIG. 1, the chambers 20, 22 are communicated by a series of apertures 26 bored through internal wall 24. These apertures 26 allow free interchange of water contained within the housing between the chambers 20, 22.

Because the phantom 10 is intended to be used in association with ionizing radiation and to provide an imaging calibration standard, the end walls 12, 14 and the side wall 16 will preferably be constructed from materials which exhibit low attenuation or which are relatively "transparent" to the ionizing radiation, at least as compared to other components of the phantom, such as the contrast or test objects which are taught herein. In selecting the specific materials for the end walls and the side wall, there are a variety of polymeric materials which will be well known to one of skill in this art, particularly the acrylic polymers.

A further feature of the first chamber 20 is a longitudinal translator in the form of a bellows 28 which is axially mounted in the first chamber. A first end of the bellows 28 is affixed to the internal wall 24 and a second end of the bellows extends outwardly into the first chamber 20 towards the first end wall 12. In the embodiment shown, the first end of the bellows comprises a bellows plate 30 and the main portion of the bellows comprises a pleated cylindrical body 32. The bellows plate 30 is affixed to the internal wall 24 by a pair of spaced apart and preferably diametrically opposed bellows stabilizer rods 34, which are threaded on a first end thereof. These threaded ends pass through apertures in the bellows plate 30 and are threadingly received in bores in the internal wall 24. The bellows stabilizer rods 34 are intended to be rigid, but they are preferably formed from a polymeric material having low attenuation, such as the polymeric material from which the phantom end and side walls are constructed. The bellows stabilizer rods 34 maintain the bellows body 32 in an essentially axial position within the first chamber 20 along the z-axis of the phantom. The purpose of the bellows 28 is to provide axial mobility for test objects (to be described more fully below) and to provide longitudinal translation of those test objects within the sealed phantom. For this reason, the bellows 28 needs to be axially extendable through most if not all of the length of the first chamber 20. Therefore, the bellows stabilizer rods 34 should also extend through most of, if not all of, the length of the first chamber 20 and the bellows body 32 must be provided with apertures through which the bellows stabilizer rods may pass from the inside of the bellows to the outside. Further apertures are provided to permit free interchange of the liquid (usually water) filling the phantom between the inside and outside of the bellows body 32. Additionally, it may be preferred to provide a means on the inner surface of the first end wall 12 to receive the ends of the bellows stabilizer rods 34.

A second end of the bellows 28 receives and retains a first end of a bellows adjustment screw 36, which has external threading and is threadingly received though an axial opening 37 having internal threading in the first end wall 12. When a second end of the bellows adjustment screw 36 is rotated, the second end of the bellows 28 moves along the z-axis within the first chamber 20, effectively lengthening or shortening the bellows. This second end of the bellows adjustment screw remains 36 external to the phantom body. The retention means used between the second end of the bellows 28 and the first end of the bellows adjustment screw 36 is such that rotation of the bellows adjustment screw does not cause rotation of the bellows body 32, but the axial movement of the adjustment screw caused by rotation causes corresponding movement in the bellows body 32 in either axial direction. In the particular embodiment shown, the axial opening 37 is provided as an cylindrical length of threading extending outwardly from the surfaces of the first end wall 12. This extension of length provides more threading for better stability of the adjustment screw 36. If the machining of the bellows adjustment screw 36 and the axial opening 37 is within close tolerances and the respective threaded surfaces are coated with an appropriate sealing lubricant, especially a water-insoluble lubricant as will be known to those of skill in the art, the water present in the phantom body will not leak out during normal operation of the adjustment screw 36.

The phantom body and the chambers formed within are normally filled with water, including the chamber internal to the bellows 28, which is provided with apertures to allow flow therethrough when the bellows is compressed or expanded. Because of this, the seal between the first end wall 12 and the flange portion 18 of the side wall 16 should be provided with a lip having an elastomeric O-ring 38 seated therein to generally prevent leakage of the water. The first end wall 12 is removably secured to the side wall 16 by fasteners, such as the bolts 40 and wing nuts 42 shown, which will be preferably composed of a non-ferrous, and even more preferably, non-metallic material, to maintain a low attenuation When the bellows adjustment screw 36 is rotated and the bellows 28 is moved, the water in the phantom may be displaced, so an overflow tube 44 is provided through the side wall 16, as well as an overflow reservoir 46 communicated to the overflow tube. Along the end pleat of the bellows body 32 at the second end thereof, it would be usual to provide a piece of a high attenuation material such as a piece of wire 48 to mark the end ridge of the bellows in the imaging process. This provides an easy means of determining the bellows position in images produced.

In addition to the basic structure of the phantom 10 already described, there are further test objects which will be used with the phantom in calibrating a CT scanner. These are now discussed. In a commercial embodiment of the invention, a kit would be provided, comprising a phantom 10 and one or more of the test objects as will now be described.

FIG. 2 shows a perspective view of a first test object 50, which is generally referred to herein as a "slice sensitivity disc." The use of this test object 50 is described further below. The slice sensitivity disc 50 is preferably a polymeric disc with a centrally positioned thin piece of circular foil 52 on one surface of the disc. The disc 50 is made from a low attenuation material and the piece of foil 52 is a high attenuation material which provides a substantially different attenuation than that of water. In use this test object 50 is preferably placed internal to the bellows 28 so that the plane of the disc 50 is essentially perpendicular to the z-axis of the phantom 10. The disc 50 will preferably contain apertures 53 through which the phantom-filling liquid may flow freely as the disc is moved within the phantom. The disc 50 may also be provided with apertures 55 for positioning the disc on the bellows stabilizer rods 34. The periphery of the disc 50 may be provided with means for attaching the disc to the bellows body 32, so that the disc may be moved longitudinally within the phantom by expanding or contracting the bellows 28. FIG. 2a shows the test object 50 being operatively engaged in the bellows 28 of the present invention.

FIG. 3 is a perspective view of a second test object 54, which is generally referred to as a "pitch effect ring" test object. This test object 54 is an annular ring, preferably composed of a polymeric low attenuation substance commonly used in the art, such as an acrylate material. The test object 54 is a thin annular disc with an inner diameter slightly larger than the diameter of the bellows body 32 and an outer diameter smaller than the side wall 16, so that the second test object may be inserted into the first internal chamber 20 outside of the bellows 28. The second test object 54 is preferably provided with a plurality of equally spaced apertures 56 of uniform diameter. In the preferred usage of the second test object 54 as described below, the second test object is fitted over and secured to the outside of the bellows body 32 in a position essentially perpendicular to the long axis of the bellows body. For this reason, the inner periphery of the test object 54 will be provided with means cooperating with means on the outside of bellows body 32 to removably attach the test object to the bellows body. FIG. 3a shows the second test object 54 being operatively engaged in the device 10 of the present invention.

FIG. 4 shows a third test object 58, which is also referred to as a "low contrast" test object. It comprises an annular ring 60 comprised preferably of a low attenuation material and at least two peripherally-attached, generally planar elements 62. Each of the peripherally-attached elements 62 is provided with a plurality of randomly placed holes of varying sizes, except that each such element has one reference hole 64, which is of a known standard diameter. The elements 62 will be preferably composed of materials having different known attenuations to simulate different tissue densities. The test utilizing this test object 58 is described further below. As with the second test object 54, the ring 60 has an inner diameter adapted to be fitted over and secured to the bellows body 32 in a position essentially perpendicular to the long axis of the bellows body. The outer diameter of the ring 60 will usually be smaller than the outer diameter of the second test object 54, so it will fit within the side wall 16 even when the planar elements 62 are attached. It is highly preferred to provide removable attachment of the planar elements 62 to ring 60 to facilitate interchange thereof.

FIG. 5 shows a perspective view of a yet fourth test object 66, which is generally referred to as a "bone ring." The test object 66 comprises a relatively narrow hoop 68 with at least one insert member 70, which is attached to the inner diameter surface of the hoop 68 and extends radially inwardly therefrom. The test object 66 is preferably used with several insert members 70, the insert members being selected to represent a variety of different attenuations, and especially to represent particular types of attenuation exhibited by specific types of bone which will be clinically encountered, such as temporal bone, occipital bone and rib bone. The materials used to simulate these bone attenuations are readily known in the art. Viewed normal to the plane of the hoop 68, the inserts 70 are preferred to provide a sharp delineation, so a triangular profile or rectangular is particularly preferred. The inserts 70 are preferred to be removably attached to the hoop 68, especially through the use of a plurality of apertures 72 bored radially through the hoop. The hoop 68 is preferably sized with an outer diameter to fit securely inside the side wall 16. Use of the bone ring test object 66 in calibrating the helical CT device is described below. In instances where all of the apertures 72 are not filled with inserts 70 representing bone attenuations, a plug 73 having an attenuation equivalent to that of the hoop 68 may be provided to fill the aperture. The external profile of certain inserts 70 and the presence of internal apertures, etc., may be used to make the particular bone attenuation reference objects visually distinctive, so that the insert is readily recognizable in the images produced.

Practitioners of the art of quality assurance and image quality validation of a computed tomographic imaging device will readily recognize the numerous potential uses of this device. Several uses are defined below. For the purposes of discussion, the image plane is designated as an "x-y" plane while the dimension perpendicular to the image plane is designated as "z".

The slice sensitivity disc 50 shown in FIG. 2 and described in the accompanying text represents an impulse in the z direction. By acquiring a series of contiguous images encompassing the disc 50, a slice sensitivity profile can be obtained by recording the CT number (as defined above) for each image at the x-y location in which the disk appears in the central images in the series. A plot of the profile can be used to calculate parameters such as slice thickness, the full-width-at-half-maximum (FWHM) and full-width-at-tenth-maximum (FWTM) as described in prior art. This test can be performed for both axial and helical scans.

Similar to low contrast testing in prior art, the low contrast test object 54 of the present invention is scanned, the hole size visibility determined and percent contrast calculated for varying diameter holes. In addition, due to the unique design of the phantom 10, the effect of locating the test object 54 at a position away from the isocenter can be studied. Unlike existing tests for low contrast, observer bias can also be eliminated by randomizing the test objects. The use of randomly oriented test patterns at locations away from the central portion of the phantom represents a more rigorous and clinically appropriate test for both helical and axial scanning systems.

In a test not involving the test objects, the CT number uniformity and noise are measured. The second internal chamber 22, which is filled with water, is scanned using the desired helical or axial scanning parameters. Regions of interest ("ROI") are selected from the displayed image data. The mean and standard deviation of each ROI are calculated via software provided by the CT scanner manufacturer as required by federal codes. The average CT numbers in each ROI are compared to examine the uniformity while the standard deviation values are used to assess the image noise.

To examine the effect of varying pitch on low contrast, a unique test methodology using the phantom 10 and the pitch effect ring test object 58 is performed. When a helical CT device is operated with the patient couch axially stationary relative to the radiation source during rotation of the radiation source and detection array, an axial image identical to the axial CT scanner is obtained. Using such an axial image as a reference, this test allows the user to measure how percent contrast is affected at various locations equidistant from the isocenter in the helical image (rev) for varying pitch ratios, as defined above. The pitch effect ring 58 is first scanned in axial mode and then re-scanned in the helical mode at different selected pitches. Using the axial data as a reference, since the percent contrast will be the same at all locations on the ring, calculated percent contrast for each of the helical data sets can be compared to the axial reference data. For convenience, data may be plotted with percent contrast on the y-axis against location on the ring on the x-axis for each data set.

Another unique test, volume scanning confirmation, confirms helical operation of a system by using a graduate scale 74 printed on the side wall 16 in association with the locator wire 48 positioned in the phantom on the bellows body 32. Once the phantom 10 is positioned such that the internal wall 24 is within the first image of the scan, the scan parameters are selected and image extent calculated. Using the surface scale 74 as a measure, the wire 48 is moved by moving the bellows 28 to the end of the image extent such that it will appear in the last image. The helical scan is made and the images are reviewed to check for the appearance of the internal wall 24 and the locators 74, 48. The locators should appear in the first and last images. This is a simple test of overall gross system functioning.

An additional test, referred to here as the interpolation effect, is an advanced and unique method by which the user may observe the effect of varying slice thickness selections and pitches on the reconstructed images. This test is performed by using one pitch effect test object 58 located some distance away from the internal wall 24 after the bellows is compressed. The internal wall 24 and the test object 58 are repeatedly scanned in the helical mode at selected pitches and slice thicknesses. Using a selected interpolator, the images are reconstructed. The distance between the internal wall 24 and the test object 58 is either decreased or increased and the process repeated until a minimum distance is determined at which a central slice between the two is not affected by the presence of either object. This unique test provides the first indicator of "slice" synthesis.

A final proposed test, referred to here as the "bone correction check", allows the user to observe the images produced by axial or helical scanning and check for the appearance for clinically relevant artifacts that can result for improper "bone correction" system software. This test may be performed with the scanner in either the helical or axial mode. With the bone ring test object 66 inserted in the phantom 10, the phantom is scanned and images examined for the appearance of artifacts which indicate poor or no bone correction.

From the above discussion, those skilled in the art will note that described herein is a phantom 10 which contains unique helical specific test functionality testing methods and which provide a measure of a system's ability to synthesis a planar image. In addition to new test objects 50, 54, 58 and 66, the phantom 10 has a unique design in that it contains a longitudinal translator 28 which allows the distance between test objects to be varied without the relocation or disassembly of the phantom as a whole. Using the described new phantom, a system's helical parameters can be examined and their effect on the resulting synthesized image studied following the tests outlined above.

While the invention has been described in detail herein in accordance with the certain preferred embodiments thereof, many modifications and changes therein may be effected by those skilled in the art. Accordingly, it is intended by the appended claims to cover all such modifications and changes as fall within the true spirit and scope of the invention.

What is claimed is:

1. A device for calibrating a computed tomography apparatus, comprising:

a housing having first and second end walls and at least one side wall;

an intermediate wall between said first and second end walls, effectively forming first and second chambers within said housing;

a longitudinal translator axially mounted within said housing, said longitudinal translator having a first end thereof axially affixed to the intermediate wall; and a longitudinal translator adjustment screw axially mounted through a threaded opening in said first end wall with a first end thereof affixed to a second end of the longitudinal translator such that rotation of a second end of the longitudinal translator adjustment screw external to the housing results in axial movement of the second end of the longitudinal translator within the housing.

2. The device of claim 1 wherein the housing is generally cylindrical with the side wall being a cylinder.

3. The device of claim 2 wherein at least the first of the end walls is removably affixed to the side wall.

4. The device of claim 3 wherein the end walls are affixable to the side wall in a water-tight manner.

5. The device of claim 1 wherein the intermediate wall is provided with at least one aperture to communicate the first and second chambers.

6. The device of claim 1 wherein the longitudinal translator is a bellows having first and second ends, a pleated generally cylindrical body between said ends, the body having apertures to communicate the inside of the bellows to the outside of the bellows.

7. The device of claim 6 wherein the bellows is supported along a longitudinal axis of the housing by at least two spaced apart bellows stabilizer rods affixed to the intermediate wall, spanning the length of the first chamber, and received in the first end wall.

8. The device of claim 6 wherein at least one pleat of the bellows body is provided with a piece of material which has a substantially higher attenuation to x-rays than the attenuation of the housing, walls, bellows and adjustment screw.

9. The device of claim 8 wherein the high attenuation piece of material is a piece of wire and the housing, walls, bellows and adjustment screw are comprised of a polymeric material.

10. The device of claim 6 wherein the exterior surface of the bellows body is adapted for affixing at least one test object thereto such that rotation of the adjustment screw results in longitudinal movement of the test object within the first chamber.

11. The device of claim 6 wherein the interior surface of the bellows body is adapted for affixing at least one test object thereto such that rotation of the adjustment screw results in longitudinal movement of the test object within the bellows body.

12. The device of claim 2 wherein the inner surface of the side wall is sized to frictionally receive and retain a generally hoop-shaped test object.

13. The device of claim 2 wherein the second chamber is an essentially hollow cylinder.

14. A test object for a computed tomography apparatus calibration device comprising:

a polymeric disc having first and second opposing surfaces with a centrally positioned circular piece of metallic foil affixed on the first surface thereof, said piece of metallic foil having an outside diameter smaller than the outside diameter of the polymeric disc.

15. The test object of claim 14 wherein the polymeric disc further comprises at least one aperture communicating the first and second surfaces thereof.

16. A test object for a computed tomography apparatus calibration device comprising:

an annular disc comprising a low attenuation material having a plurality of equally spaced apart apertures of uniform diameter passing through the disc from a first planar surface thereof to an opposing second planar surface; and an inside periphery of the annular disc being adapted for affixation to a cylindrical body having an outside diameter slightly smaller than the inside diameter of said annular disc.

17. A test object for a computed tomography apparatus calibration device comprising:

an annular disc having an inside diameter and an outside diameter, the periphery at said outside diameter having at least two apertures for removably affixing planar test elements of a known attenuation value, each said planar test element further having at least one aperture passing therethrough with one of said at least one aperture being of a known diameter; and an inside periphery of the annular disc being adapted for affixation to a cylindrical body having an outside diameter slightly smaller than the inside diameter of said annular disc.

18. A test object for a computed tomography apparatus calibration device comprising:

a generally hoop-shaped disc having an inside diameter and an outside diameter and comprising a material of known attenuation, the inside diameter having a plurality of radially oriented apertures for removably affixing along said inside diameter at least one test element of a known attenuation value simulating a type of human bone, wherein each such test element has a male member for insertion in said aperture in a frictional fit and a visually distinctive profile dependent upon the attenuation value.

19. A computed tomography apparatus calibration test kit comprising the device of claim 1 and at least one of the devices of claims 14, 16, 17 and 18.

* * * * *